United States Patent [19]

Sander et al.

[11] Patent Number: 5,037,445
[45] Date of Patent: Aug. 6, 1991

[54] METHOD AND KIT FOR MOLDING SURGICAL IMPLANTS

[75] Inventors: Thomas Sander, Newtown; Robert D. Torgerson, Branford, both of Conn.

[73] Assignee: United States Surgical Corporation, Norwalk, Conn.

[21] Appl. No.: 337,908

[22] Filed: Apr. 14, 1989

[51] Int. Cl.$^5$ .................................................. A61F 2/30
[52] U.S. Cl. ...................................... 623/66; 623/16; 264/101
[58] Field of Search .......................... 623/11, 16, 66, 6; 264/101, 102, 126, 571; 433/201.1, 228.1, 212.1

[56] References Cited

U.S. PATENT DOCUMENTS

| | | | |
|---|---|---|---|
| 3,705,248 | 12/1972 | Hill et al. | 264/571 X |
| 3,954,931 | 5/1976 | Helmuth et al. | 264/571 |
| 4,031,179 | 6/1977 | Tatzel et al. | 264/102 X |
| 4,452,776 | 6/1984 | Refojo | 623/66 X |
| 4,473,423 | 9/1984 | Kolff | 264/571 X |
| 4,535,485 | 8/1985 | Ashmann et al. | |
| 4,536,158 | 8/1985 | Bruins et al. | |
| 4,728,570 | 3/1988 | Ashman et al. | |

FOREIGN PATENT DOCUMENTS 2069917  9/1981  United Kingdom .

*Primary Examiner*—Alan Cannon
*Attorney, Agent, or Firm*—Thomas R. Bremer

[57] ABSTRACT

A vacuum bag method for in-situ molding of surgical implants. The method comprises creating an implant precursor material composed of an aggregation of polymer beads coated with a hydrophilic monomer dispersion. A flexible bag containing the implant precursor is molded in-situ to a desired specific shape, and the implant precursor is then rigidified by applying a vacuum to the interior of the bag. The implant precursor is cured by heating to form a unitary porous prosthesis which may be implanted into body tissue to remedy bone defects.

42 Claims, 2 Drawing Sheets

METHOD AND KIT FOR MOLDING SURGICAL IMPLANTS

BACKGROUND OF THE INVENTION

1. Field Of The Invention

This invention relates to a method for molding surgical implants and more particularly relates to a vacuum technique for molding an implant of polymer beads.

2. Description Of The Prior Art

In certain surgical applications such as prosthetic implantation to fill bone defects caused by trauma, tumor resection, congenital defects, infections, etc., it is desirable to have a prosthetic implant which can be molded to any desired shape. Ideally, such an implant should be porous to allow for bone growth, malleable to allow it to conform to various shapes, yet firm and rigid when fixed to the bone to provide for a strong, solid support.

A material which has been used successfully in bone implantation is described in Ashman et al. U.S. Pat. Nos. 4,728,570 and 4,535,485, and in Bruins et al. U.S. Pat. No. 4,536,158. The material disclosed therein is a conglomerate of polymethylmethacrylate beads coated with polyhydroxyethylmethacrylate. The beads may be joined into a unitary structure as disclosed in U.S. Pat. No. 4,536,158, or they may be used in granular form as disclosed in U.S. Pat. No. 4,535,485.

When used as granules, the beads are packed into a cavity, such as the cavity in the gums remaining after a tooth extraction, and the cavity is sewn closed. When used as a unitary porous mass a separate mold must be fabricated based on the extracted tooth. The mold is then filled by packing it with the polymer beads which have been wetted with polyhydroxyethylmethacrylate, and heated in a dielectric oven to polymerize and/or sinter the beads into a unitary porous mass.

Such techniques are useful in dental procedures like tooth extraction where it is possible to fill a void, or to make a separate mold based on an extracted tooth. In other applications, however, it is not possible to make a separate mold, or to pack a cavity and sew it closed. Certain procedures, such as augmentation of bony structures for cosmetic purposes, or implantation to fill bone defects, require the implantation of a unitary structure which has been custom shaped in situ, i.e., which as been molded within the surgical site where it will be implanted. In situ shaping of implant material is not possible with the modalities disclosed by the above-mentioned references.

SUMMARY OF THE INVENTION

Accordingly, it is one object of the present invention to provide a method for molding a surgical implant.

It is another object of the present invention to provide a method for molding a surgical implant which allows the implant to be shaped in situ.

It is yet another object of the present invention to provide a method for molding a porous surgical implant for bone.

A still further object of this invention is to provide a method for implanting a custom molded prosthesis in body tissue.

These and further objects are achieved herein by providing a method for custom molding an implantable prosthesis for hard tissue, said method comprising:

a) providing an implant precursor within a flexible bag, said implant precursor comprising an aggregation of individual particles of a structural material which is biocompatible after being cured;

b) forming said bag of implant precursor to a specific shape;

c) compacting the implant precursor into a rigid mass having said specific shape by applying a vacuum to the interior of the bag; and d) curing the implant precursor to provide porous unitary prosthesis having said specific shape.

Further provided herein is a method for implanting a custom molded prosthesis into body tissue comprising:

a) providing an implant precursor within a flexible bag, said implant precursor comprising an aggregation of individual particles of a structural material which is biocompatible after being cured;

b) forming said bag of implant precursor to a specific shape;

c) compacting the implant precursor into a rigid mass having said specific shape by applying a vacuum to the interior of the bag;

d) curing the implant precursor to provide porous unitary prosthesis having said specific shape;

e) optionally removing said bag from the prosthesis; and, f) implanting said prosthesis into body tissue.

DETAILED DESCRIPTION OF THE INVENTION

Figure 1:
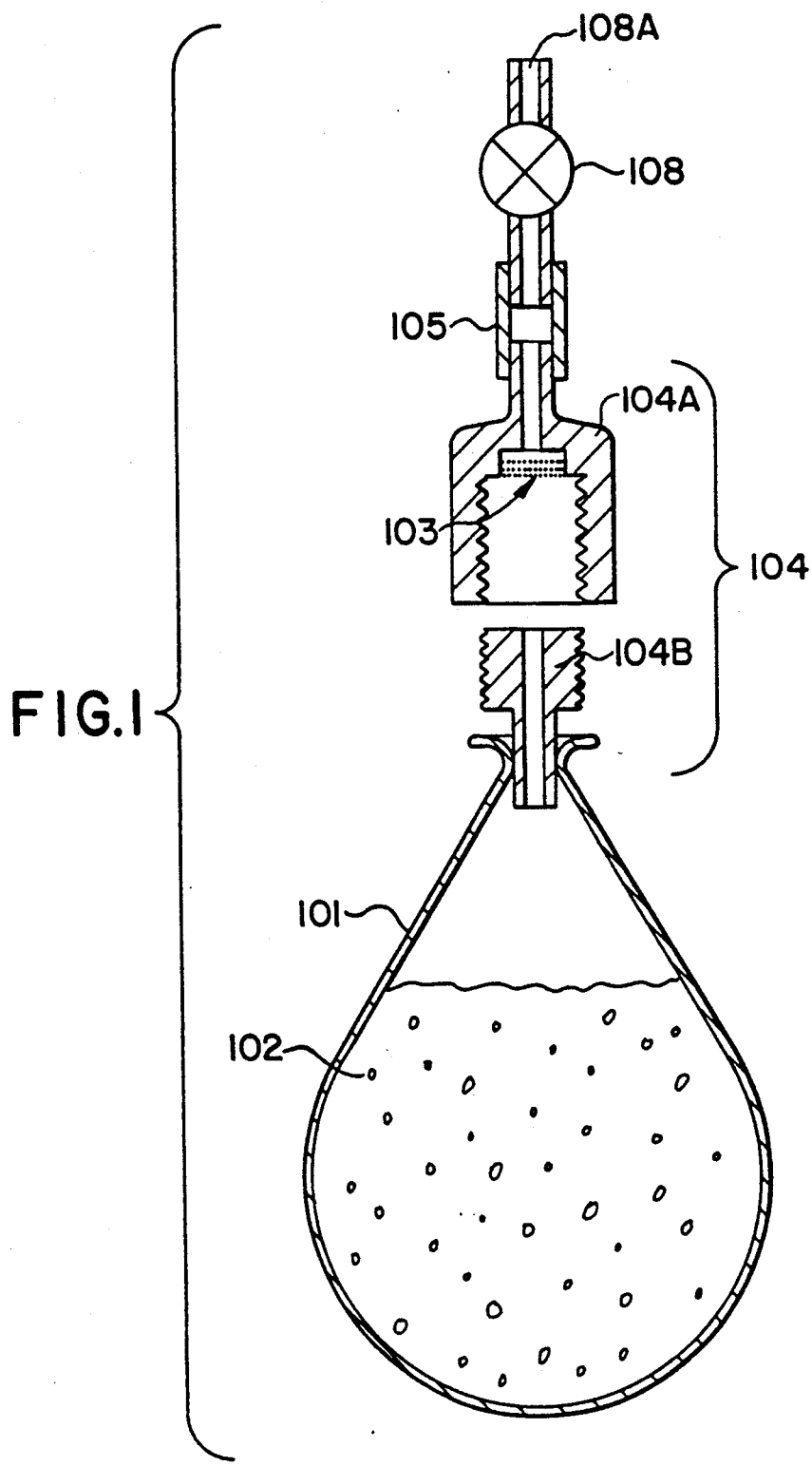
FIG. 1 is a diagrammatic illustration of the custom molding apparatus employed in carrying out the molding process of the present invention; and, FIG. 2 is a diagrammatic illustration of an alternative embodiment of the custom molding apparatus.

In accordance with the present invention, a porous prosthesis for filling bone defects is molded in situ employing an aggregation of polymeric beads. Polymeric beads useful in this procedure of the present invention are described in Bruins et al., U.S. Pat. No. 4,536,158, and in Ashman et al., U.S. Pat. Nos. 4,535,485 and 4,728,570, all of which are incorporated by reference herein.

The terms "biocompatible" and "biologically compatible" are used interchangeably herein and refer to materials or devices which, when implanted in a living body, do not cause rejection, infection, inflammation, or other such adverse body reaction. The term "bioabsorbable" as used herein refers to materials which can be decomposed and/or absorbed by body tissue.

The molding method of the present invention comprises several basic steps, the first being the providing of an implant precursor inside a flexible bag. The flexible bag must be conformable to the particularly desired shape of the finished prosthesis. The implant precursor comprises an aggregation of individual particles of a structural material, and it (the implant precursor) must be potentially biocompatible, i.e., the implant precursor may or may not be biocompatible before curing, but after curing the implant precursor must form a biocompatible prosthesis. Also, the cured implant material can be either bioabsorbable or permanent.

One such structural material which has been found useful is polymethylmethacrylate (PMMA). The preferred size of the aforementioned particles is 20–24 mesh. This particle size will produce a unitary porous mass having a pore size in the range of 200 to 400 microns, which is suitable for bone ingrowth. Other particle sizes can be used to obtain prosthesis with alternative pore sizes. For example, 40 to 60 mesh PMMA particles will result in a prosthesis with pore sizes of about 125 to 210 microns, which are suitable for soft tissue ingrowth, but not bone ingrowth.

Other agents may optionally be added as part of the implant precursor. For example, the particles of potentially biocompatible structural material (such as PMMA) may be coated with a monomeric second material which can be polymerized into a biologically compatible, hydrophilic polymer coating. The polymer coating serves to bond together the particles of structural material. The hydrophilic properties facilitate the ingrowth of body tissue. As a specific example, a structural material comprising PMMA beads may be coated with hydroxyethylmethacrylate (HEMA), which is subsequently polymerized into polyhydroxyethylmethacrylate (PHEMA), a biocompatible hydrophilic polymer.

Optionally included with the monomer are: crosslinking agents, such as triethyleneglycol dimethylacrylate (TEGDMA); polymerization initiators, such as benzoyl peroxide; and, radio opaque substances, such as barium sulfate; or other materials conducive to the treatment of the patient. The hydrophilic coating allows greater penetration by body fluids into the prosthesis, thereby aiding bone ingrowth. The monomer coating material with any other dispersed additives, must be mixed well with the particles of structural material to form an even coating on all the particles. This mixing of coating material and structural material may be done within the flexible bag, or prior to adding the implant precursor mixture to the bag.

At this stage the implant precursor is an unshapen malleable mass of individual particles which, having air spaces between them, are far enough from each other to allow for mobility, and they flow like sand.

In the second step, the bag containing the implant precursor is formed into a specifically desired shape. Usually, this is done in situ, i.e., the surgeon fits the bag into a bony defect within the body tissue, and conforms the bag to the shape of the defect. It may be advantageous to draw a light vacuum on the bag to facilitate the molding of the bag by the surgeon.

Thirdly, the implant precursor is compacted into a rigid mass by applying a vacuum to the interior of the bag.

Fourth, the implant precursor is cured, thereby setting the implant precursor and providing a unitary porous prosthesis which retains the specifically shape into which it was previously formed. The curing process comprises any process or combination of processes which bond together the individual particles of structural material. Such curing processes include, but are not limited to sintering and/or polymerization. For example, if PMMA particles are used alone as the implant precursor, curing can be accomplished by sintering. If a monomer coating such as HEMA is employed, the curing process includes polymerizing the coating to bond the particles together. Both sintering and polymerization may be employed together, or as alternative methods of curing.

Sintering and/or polymerization may be accomplished by heating the implant precursor as, for example, by dielectric heating using radio frequency or microwaves, or by convection or radiant thermal heating.

As a fifth step after curing, the bag is generally removed from the prosthesis. However, it is also within the purview of the present invention to employ a biodegradable bag, thereby eliminating the necessity of removing the bag from the prosthesis. Optionally, an additional washing step may be employed to remove residual monomer. After washing various agents conducive to healing may be added as, for example, bone growth promoters such as calcium hydroxide, growth factors, blood, antibiotics and combinations thereof.

FIG. 1 illustrates a vacuum molding apparatus 100 according to the present invention. Bag 101 is a flexible, medical grade material capable of withstanding temperatures in excess of the sintering temperature of the implant material, and is not affected by the heating method used to cure the implant precursor. Such material may be, for example, fluorocarbon polymer sheeting or latex. Within the bag is an implant precursor in the form of an aggregation of individual particles 102 of a potentially biologically compatible structural material, such as polymethylmethacrylate (PMMA) with or without the monomer coating and additives indicated above. If monomer and additives are employed, they must be agitated to create a well mixed dispersion and then added to the particles of structural material, which is then kneaded to coat substantially all of the particles. The implant precursor can be prepared within the flexible bag 101, or outside of the bag 101 and subsequently injected therein.

Flexible bag 101 is connected to an adapter 104 which comprises top portion 104A and bottom portion 104B.

The adapter portions are threaded—one externally, the other internally—so that they can be removably screwed together. Adapter 104 is connected to one-way valve 108 by means of a connecting tube 105. Adapter 104 allows a vacuum to be applied to the inside of bag 101. Screen 103 has a mesh size small enough to prevent the particles 102 from being drawn out by the vacuum. Outlet 108A is connected to the inlet of a vacuum pump (not shown). One way valve 108 permits air or vapor to be withdrawn from the apparatus 100 through outlet 108A when the vacuum is applied, but it prevents air from reentering through outlet 108A when the vacuum is no longer applied, thereby maintaining the vacuum inside the apparatus 100 when outlet 108A is disconnected from the vacuum pump.

The surgeon inserts the bag 101 into the bony defect on the patient, then molds it to a specifically desired shape either by hand or with the aid of surgical instruments. It may be desirable to draw a light vacuum on the bag to facilitate this process. When the desired shape has been attained the surgeon compacts the implant precursor into a rigid mass with said specific shape by applying a vacuum to the interior of the bag 101. This is accomplished by withdrawing the air by means of a vacuum pump attached to outlet 108A. When the air is withdrawn from the interior, the particles of implant precursor material 102 are pressed closer together by the outside air pressure. This eliminates the interstitial space which provided freedom of movement and thereby rigidifies the aggregation of particles 102 in whatever shape the bag 101 was molded into. The vacuum pump may then be removed. One way valve 108 will maintain the vacuum after the pump is disconnected. As indicated above, the next step is to create a porous unitary prosthesis with the desired shape by curing the implant precursor. This can be accomplished, for example, by subjecting the apparatus 100 to microwave heating.

After the curing process has been completed, the prosthesis is allowed to cool, and the bag 101 is removed from the prosthesis by cutting it away.

The prosthesis is now prepared and can be implanted into body tissue. However, as an optional additional step before implantation, the prosthesis may be washed, for example in boiling saline solution. Also, bone growth promoters such as calcium hydroxide, growth factors, blood, and/or antibiotics, can be introduced into the porous structure of the prosthesis after the prosthesis has been washed.

Using this method, a surgeon can begin implanting the custom molded prosthesis into body tissue within a few minutes after beginning the operation.

Figure 2:
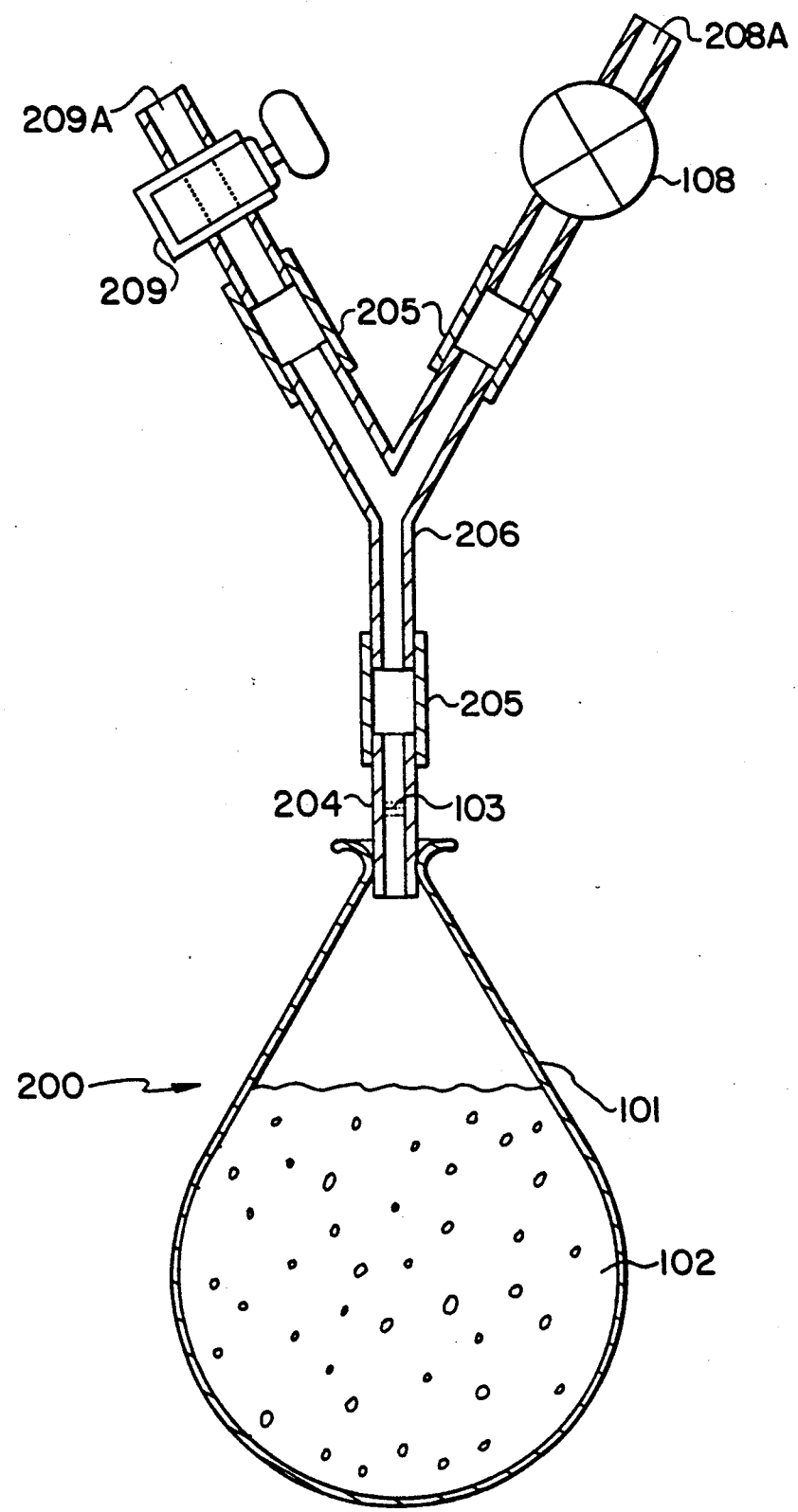

FIG. 2 illustrates an alternative apparatus 200 used in conjunction with this invention.

Flexible bag 101 contains implant precursor material 102, i.e., particles of potentially biocompatible structural material. Bag 101 is connected to adapter 204. Screen 103 has a mesh size small enough to prevent particles 102 from being withdrawn from the bag 101 when a vacuum is applied via opening 208A. Y-Adapter 206 provides two channels: one for applying a vacuum, and one for introducing a monomer coating material. Connecting tubes 205 connect the Y-adapter 206, to adapter 204, to stopcock 209, and to one way valve 108.

In an alternative embodiment of the present invention the biologically compatible structural material, is provided within flexible bag 101. A monomer coating material such as described above, together with optionally mixed additives, is injected by means of a syringe (not shown) to the apparatus 200 in FIG. 2 via inlet 209A with stopcock 209 in the open position. As an aid to the injection of the mixture, a vacuum may be preapplied by means of a vacuum pump (not shown) to the opening 208A. The vacuum is maintained temporarily until the coating mixture has been added. Enough monomer coating mixture is added to coat substantially all of the particles 102 in flexible bag 101. Once the mixture has been added, the flexible bag 101 is kneaded by hand for about two minutes to fully coat substantially all of the particles 102. The preparation of the implant precursor is now completed and the surgeon may proceed to the next step, i.e., forming the bag 101 containing the implant precursor 102 to a specific shape. This is accomplished by inserting the bag 101 into the bony defect, then shaping it by hand or with the aid of surgical instruments.

After the desired shape has been attained the surgeon compacts the bag by applying a vacuum to the interior of bag 101 via opening 208A. Stopcock 209 is in the closed position, and one way valve 108 will maintain the vacuum when after the vacuum pump is disconnected. As explained above, the vacuum compacts and rigidifies the aggregation of implant precursor 102 into whatever desired specific shape the surgeon formed.

Having completed the forming and vacuum rigidification steps, the surgeon sets the implant precursor in the specifically desired shape. This can be done by bonding the aggregation of particles 102 by the methods indicated above. Under microwave heating, for example, the monomer, such as HEMA, will polymerize into a hydrophilic coating, such as PHEMA, which is firmly bonded to the particles 102 of biocompatible structural material, such as PMMA.

As discussed above, after the setting process has been completed, the prosthesis is allowed to cool, and the bag 101 is typically removed from the prosthesis by cutting it away. The necessity of removing the bag may be eliminated, however, if a biodegradable bag is employed.

Next, the prosthesis is washed in boiling saline solution for about two minutes to remove residual monomer, and optional bone growth promoters such as calcium hydroxide, or other medicinal or healing agents may be then incorporated into the porous prosthesis. The prosthesis is now prepared. Finally, the surgeon can now begin implanting the custom molded prosthesis into the bony defect within a few minutes after beginning the operation.

The following are two examples of procedures which illustrate in detail the method for preparing and applying the technique of the present invention for in-situ molding of surgical implants.

With respect to method using the Y adapter apparatus as shown in FIG. 2, the bag 101 is formed by dip molding medical grade latex resulting in a thickness of ranging from 0.006" to 0.010".

The latex bag is filled with polymethylmethacrylate beads (PMMA) ranging in size from 700 to 850 microns (20/24 mesh.) The bag is filled by placing a plastic or glass funnel (with an opening of the funnel mouth equivalent to the opening of the bag) into the mouth of the bag and then pouring the PMMA beads through the funnel into the bag. When filling the bag one should leave enough room within the bag to insert the adapter 204. For example, the amount of PMMA beads 102 can be about 15 grams to fill the bag 101. The y-connector for the fill and vacuum line is assembled by placing a nylon screen 103 in or over the adapter 204. The adapter 204 can be injection molded around the nylon screen 103 so the screen will not be drawn out of the apparatus. The adapter 204 is inserted into latex tubing 205, which has a ¼ inch outer diameter. The other open end of the latex tubing 205 is attached to the y-adapter 206 with the two openings that are 45° from each other facing in opposite the direction. The y-adapter 206 is a y-shaped tubing connector made of polypropylene with a ¼ inch outer diameter. Latex tubing 205 is attached to each of the other two ends of the y-adapter 206. The length of the latex tubes 205 can range from ½ to 2 inches.

One should then attach a duck-bill valve 108, for example a VERNAY SUPRAVALVE, to one end of the latex tubing 205 making sure that the one way duck-bill valve points away from the balloon or bag 101. The one-way valve will allow air or gas to exit but not enter the bag, and it can not only be used when evacuating the system but also as a relief valve to expel any gases that are created during the curing process. One should also attach a one-way stopcock with a two finger handle 209 to the other piece of latex tubing 205. The one way stopcock 209 is a high pressure stopcock made up of high grade polycarbonate resin. Therefore, from the y-connector 206 there should be a latex bag 101, a one-way stopcock 209 and a duck-bill valve 108 with latex tubing 205 separating them from the y-connector.

The hydroxyethylmethacrylate/triethylene glycol dimethacrylate mixture (HEMA/TEGDMA) is packaged by aseptic fill into a 10 cc luer-lock plastic syringe. The syringe should contain 15 parts by weight for every 100 parts PMMA and the HEMA/TEGDMA mixture is about 97.5% by weight HEMA, and 2.5% by weight TEGDMA. A cap is placed onto the end of the syringe to keep the mixture within the syringe.

Barium sulfate (3% by weight of the total amount of PMMA beads 102 is packaged into an amalgamator capsule along with 0.3% by weight of 78% benzoyl peroxide. A pestle is placed into the capsule to insure a complete mixing of ingredients when the HEMA/TEGDMA mixture is added. A saturated solution of calcium hydroxide solution (pH: 12 to 13) is packaged into a polyethylene vial and capped off with a blanket of dry nitrogen gas. The vial contains 50 ml of solution. The capsule and vial may be packaged into separate tyvek pouches and sterilized by gamma radiation such as a 2.5 to 3.5 megarad dose from a cobalt-60 gamma ray source. The loaded 10 cc luer-lock syringe containing the HEMA/TEGDMA mixture can be sterilized preferably with ethylene oxide.

The apparatus is then ready to be transported to the operating area for use in the vacuum molding process. To use the apparatus for custom molding a prosthesis, the surgeon attaches a vacuum line to end 208A of the one-way valve 108, making sure that the stopcock 209 is in the closed position. The surgeon then applies a vacuum to the apparatus and, preferably, checks the apparatus for leaks.

The next step is for the surgeon to expel the HEMA/TEGDMA mixture from the luer-lock syringe into the capsule containing barium sulfate and benzoyl peroxide. The capsule is then agitated for about 20 seconds to create a dispersion. The dispersion is then drawn back up into the syringe and the syringe then attached to the end 209A of stopcock 209. When the stopcock 209 is opened, the vacuum will draw the HEMA/TEGDMA dispersion into the bag. The surgeon then blends the ingredients by carefully kneading the latex bag 101 making sure not to puncture the walls. He kneads the bag for 5 minutes and then places the bag into the surgical site or cavity to receive the implant. Applying a vacuum once again by attaching a vacuum line to the end of the valve 108A, he molds the bag into the site while the vacuum is being drawn to create a custom part out of polymer.

When the shaping of the bag has been completed the vacuum line is removed from the one-way valve 208 and the entire apparatus 200 is placed in a microwave oven and cured for two to three minutes while the vacuum is maintained within the bag 101.

After curing is completed the apparatus 200 is removed from the oven, and the latex bag is cut away from the cured prosthesis, which is then immersed in boiling sterile saline solution for 5 minutes to remove residual monomer.

The prosthesis is placed in the vial containing calcium hydroxide solution and allowed to soak for 15 minutes. It is then removed and rinsed. The prosthesis is now ready to be implanted.

Referring now to FIG. 1, the following description outlines in detail another embodiment of the present invention.

The latex bag 101 is formed as discussed in the y-connector technique.

A two piece adapter 104 is made from nylon. The top portion 104A can be removed from the bottom portion 104B by unscrewing it, thereby allowing access into the bag. The bottom portion 104B (male threaded) has a ¾ inch outer diameter with a 9/16 inch inner diameter. The top portion 104A has a ¾ inch inner diameter with a 13/16 inch outer diameter and a ½ inch length. The top portion 104A has a shape adapted to receive a 1/8 inch inner diameter latex tubing. The bottom portion 104B is attached to the latex bag. The top portion 104A should contain a nylon screen molded into it to keep the PMMA beads from being drawn from the surgical adapter component 104 (FIG. 1). The screen mesh should be 100 to 300 microns in size.

A 0.25 inch outer diameter latex tube 105, which has a length of about ½ inch to 2 inches, is attached to the top of the nylon adapter 104. A one-way valve 108 is attached to the end of the latex tubing.

The PMMA beads 102 are packaged into a 60 ml capacity polyethylene vial with a cap. 15 grams of material are placed into the vial and sealed. The PMMA beads are sterilized in the same manner as outlined in the previously described embodiment. The HEMA/TEGDMA dispersion with barium sulfate and benzoyl peroxide is prepared as described above.

To use the device for custom molding the ingredients are blended as outlined above. The HEMA/TEGDMA dispersion is poured into the vial containing the PMMA beads and mixed thoroughly for 2 minutes using a sterile spatula to form an implant precursor 102. The implant precursor mixture is then drawn up in a luer-lock syringe and then injected into the bag 101 via bottom portion 104B. The top portion 104A is then screwed onto the bottom portion.

As described above the implant precursor 102 in bag 101 is then molded to a specific shape, rigidified by vacuum and cured to form a prosthesis. Also, the prosthesis is removed from the bag 101, boiled in saline solution and impregnated with calcium hydroxide solution as described above.

Surgeons or other users may be provided with a kit for use in the custom molding process of the present invention. Such a kit includes:

a) a quantity of polymethyl methacrylate particles, or beads;

b) a solution of hydroxyethymethacrylate and triethyleneglycol dimethacryalte;

c) a flexible bag with a one way valve;

d) optionally a quantity of benzoyl peroxide and/or barium sulfate.

e) optionally, a solution of one growth promoter such as a calcium hydroxide, and/or growth factor or antibiotic;

f) optionally, a funnel g) optionally, a container for boiling the prosthesis.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A method for custom molding an implantable prosthesis, comprising:
   a) providing an implant precursor material within a flexible bag, said implant precursor material comprising an aggregation of individual particles of a structural polymeric material which is biocompatible after being cured;
   b) forming said bag of implant precursor material into a specific shape;
   c) compacting the implant precursor material into a rigid mass having said specific shape by applying a vacuum to the interior of the bag;

d) curing the implant precursor material to provide a porous unitary prosthesis having said specific shape; and e) removing the bag from the prosthesis.

2. The method of claim 1 wherein the particles of the structural material each have an outer coating of a second material containing a monomer which is polymerizable into a biologically compatible hydrophilic polymeric material.

3. The method of claim 2 which additionally comprises washing the prosthesis to remove residual monomer.

4. The method of claim 1 wherein the polymeric structural material is polymethylmethacrylate.

5. The method of claim 1 wherein said curing comprises at least one method selected from the group consisting of sintering and polymerizing.

6. The method of claim 5 wherein the sintering and polymerization is accomplished by heating.

7. The method of claim 6 wherein the heating comprises at least one method selected from the group consisting of microwave heating, radio frequency heating, convection heating, and radiant heating.

8. The method of claim 1 wherein the prosthesis is bioabsorbable.

9. The method of claim 2 wherein said monomer is hydroxyethylmethacrylate.

10. The method of claim 2 wherein said second material additionally contains a radio-opaque substance.

11. The method of claim 10 wherein said radio-opaque substance is barium sulfate.

12. The method of claim 3 which additionally comprises incorporating at least one material into the porous prosthesis after the prosthesis has been washed, said material being selected from the group consisting of a bone growth promoter, a growth factor, blood and an antibiotic.

13. The method of claim 12 wherein said bone growth promoter is calcium hydroxide.

14. The method of claim 2 wherein said second material contains a crosslinking agent.

15. The method of claim 14 wherein said crosslinking agent is triethyleneglycol dimethacrylate.

16. The method of claim 2 wherein said second material contains a polymerization initiator.

17. The method of claim 16 wherein said polymerization initiator is benzoyl peroxide.

18. The method of claim 1 wherein the particles of the structural material have diameters ranging from about 590 to 700 microns.

19. The method of claim 1 wherein the flexible bag is made from a material selected from the group consisting of fluorocarbon polymer sheeting and latex.

20. The method of claim 2 wherein the second material comprises a dispersion of barium sulfate and benzoyl peroxide in hydroxyethylmethacrylate and triethyleneglycol dimethacrylate.

21. The method of claim 3 wherein the washing of said implant is accomplished in boiling saline solution.

22. The method of claim 1 wherein said bag is biodegradable.

23. A method for custom molding an implantable prosthesis for hard tissue comprising:

a) providing an implant precursor within a flexible bag, said implant precursor comprising an aggregation of individual particles of polymethylmethacrylate, said particles each having an outer coating comprising a dispersion of barium sulfate and benzoyl peroxide in hydroxyethylmethacrylate and triethyleneglycol dimethacrylate, b) forming said bag of implant precursor to a specific shape, c) compacting the implant precursor into a rigid mass having said specific shape by applying a vacuum to the interior of the bag;

d) providing a porous, unitary and porous prosthesis having said specific shape by curing the implant precursor material;

e) removing said bag from the prosthesis;

f) washing said implant in boiling saline solution to remove residual monomer;

g) incorporating calcium hydroxide into the prosthesis for promoting bone growth.

24. A method for custom molding an implantable prosthesis, comprising:

a) providing an implant precursor material within a flexible bag, said bag being biodegradable, said implant precursor material comprising an aggregation of individual particles of a structural polymeric material which is biocompatible after being cured;

b) forming said bag of implant precursor material into a specific shape;

c) compacting the implant precursor material into a rigid mass having said specific shape by applying a vacuum to the interior of the bag;

d) curing the implant precursor material to provide a porous unitary prosthesis having said specific shape.

25. The method of claim 24 wherein the particles of the structural material each have an outer coating of a second material containing a monomer which is polymerizable into a biologically compatible hydrophilic polymeric material.

26. The method of claim 25 which additionally comprises washing the prosthesis to remove residual monomer.

27. The method of claim 26 wherein the polymeric structural material is polymethylemthacrylate.

28. The method of claim 24 wherein said curing comprises at least one method selected from the group consisting of sintering and polymerizing.

29. The method of claim 28 wherein the sintering and polymerization is accomplished by heating.

30. The method of claim 29 wherein the heating comprises at least one method selected from the group consisting of microwave heating, radio frequency heating, convection heating, and radiant heating.

31. The method of claim 24 wherein the implant material is bioabsorbable.

32. The method of claim 26 which additionally comprises incorporating at least one material into the porous prosthesis after the prosthesis has been washed, said material being selected from the group consisting of a bone growth promoter, a growth factor, blood and an antibiotic.

33. The method of claim 26 wherein said monomer is hydroxyethylmethacrylate.

34. The method of claim 32 wherein said bone growth promoter is calcium hydroxide.

35. The method of claim 25 wherein said second material contains a crosslinking agent, said crosslinking agent is triethyleneglycol dimethacrylate.

36. The method of claim 25 wherein said second material contains a polymerization initiator.

37. The method of claim 36 wherein said polymerization initiator in benzoyl peroxide.

38. The method of claim 24 wherein the particles of the structural material have diameters ranging from about 590 to 700 microns.

39. The method of claim 24 wherein the second material comprises a dispersion of barium sulfate and benzoyl peroxide in hydroxyethylmethacrylate and triethyleneglycol dimethacrylate.

40. The method of claim 26 wherein the washing of said implant is accomplished in boiling saline solution.

41. A method for implanting a custom molded prosthesis into body tissue comprising:
 a) providing an implant precursor material within a flexible bag, said bag being biodegradable, said implant precursor material comprising an aggregation of individual particles of a structural polymeric material which is biocompatable after being cured;
 b) forming said bag of implant precursor material into a specific shape;
 c) compacting the implant precursor material into a rigid mass having said specific shape by applying a vacuum to the interior of the bag;
 d) curing the implant precursor material to provide a porous unitary prosthesis having said specific shape; and
 e) implanting said prosthesis into body tissue.

42. A method for implanting a custom molded prosthesis into body tissue comprising:
 a) providing an implant precursor material within a flexible bag, said implant precursor material comprising an aggregation of individual particles of a structural polymeric material which is biocompatable after being cured;
 b) forming said bag of implant precursor material into a specific shape;
 c) compacting the implant precursor material into a rigid mass having said specific shape by applying a vacuum to the interior of the bag;
 d) curing the implant precursor material to provide a porous unitary prosthesis having said specific shape;
 e) removing said bag from the prosthesis; and
 f) implanting said prosthesis into body tissue.

* * * * *